United States Patent [19]

MacAnally et al.

[11] Patent Number: 4,846,154
[45] Date of Patent: Jul. 11, 1989

[54] DUAL VIEW ENDOSCOPE

[76] Inventors: Richard B. MacAnally, 6002 Flagstaff, Star Rte., Boulder, Colo. 80302; Charles D. Cawood, 11527 N. Lou Al Ct., Houston, Tex. 77024

[21] Appl. No.: 205,667

[22] Filed: Jun. 13, 1988

[51] Int. Cl.$^4$ .............................................. A61B 1/06
[52] U.S. Cl. ...................................... 128/6; 350/174; 350/352
[58] Field of Search ........................... 128/4, 5, 6, 7, 8; 350/169, 174, 352, 573, 173

[56] References Cited

U.S. PATENT DOCUMENTS

| | | | |
|---|---|---|---|
| 2,403,731 | 7/1946 | MacNeille | 88/65 |
| 3,711,181 | 1/1973 | Adams et al. | 350/157 |
| 3,918,438 | 11/1975 | Hayamizu et al. | 128/4 |
| 4,066,334 | 1/1978 | Fray et al. | 350/160 |
| 4,148,550 | 4/1979 | MacAnally | 350/54 |
| 4,148,551 | 4/1979 | MacAnally | 350/54 |
| 4,398,811 | 8/1983 | Nishioka et al. | 128/7 X |
| 4,699,463 | 10/1987 | D'Amelio et al. | 128/4 X |

Primary Examiner—William H. Grieb
Attorney, Agent, or Firm—Tilton, Fallon, Lungmus

[57] ABSTRACT

An endoscope which is provided at its distal end with two fixed field lens assemblies, one facing generally forwardly and the other laterally, the endoscope also being provided with an adjustable control allowing the practioner to switch at will between the illuminated surgical or diagnostic site as viewed by one field lens or the other without removing the endoscope from the patient.

20 Claims, 2 Drawing Sheets

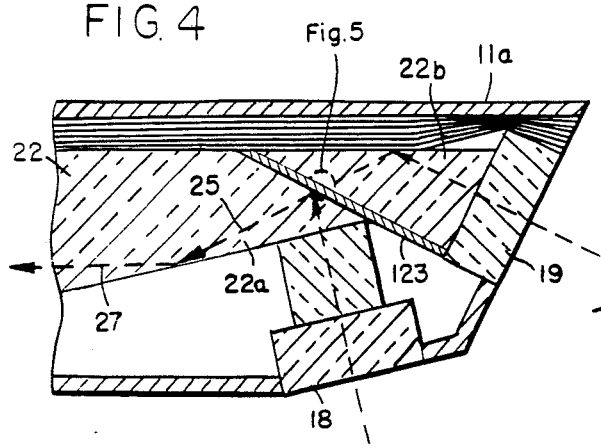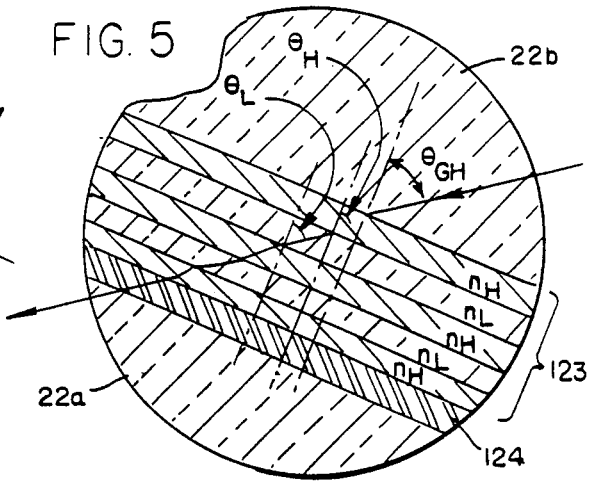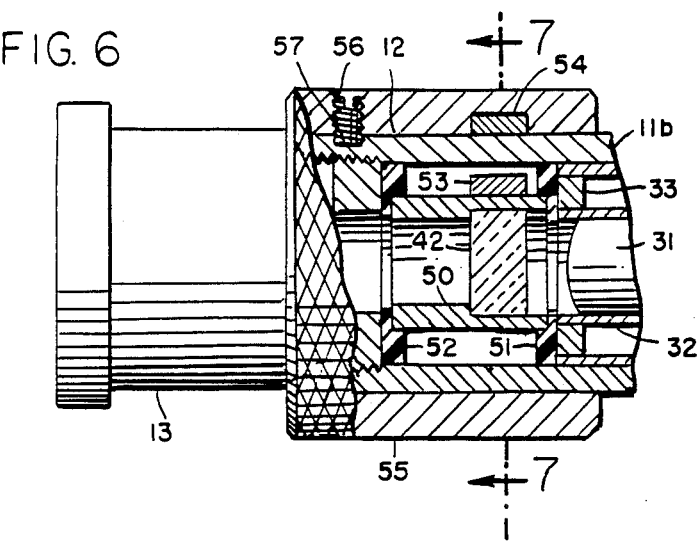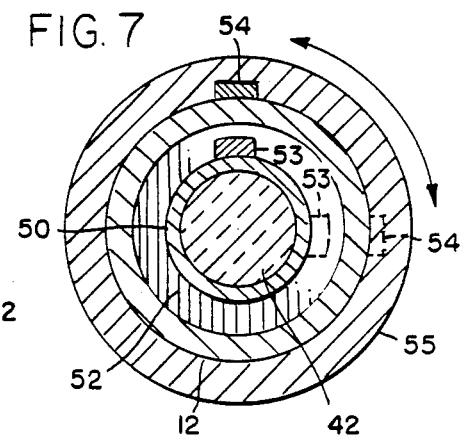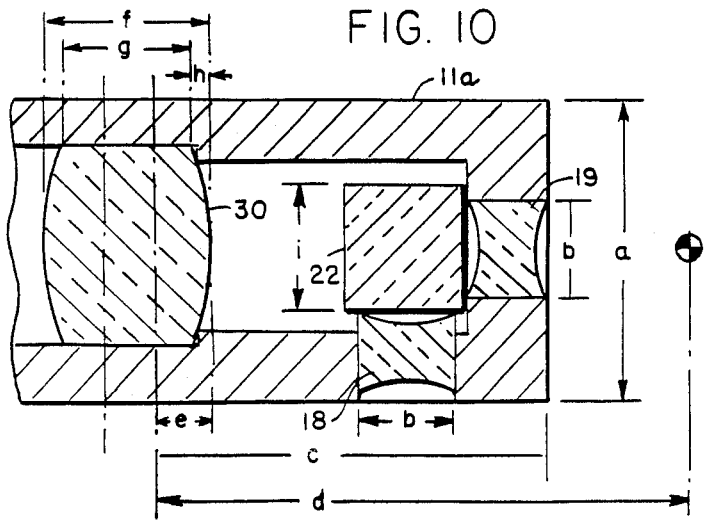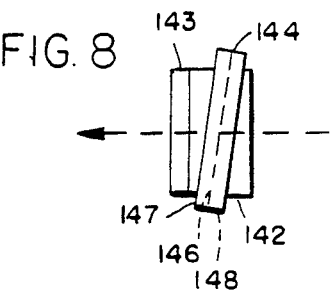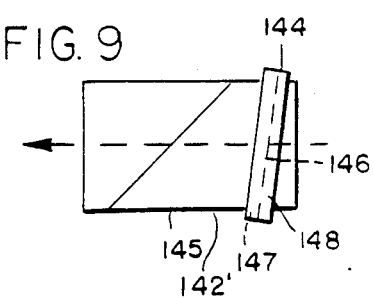

DUAL VIEW ENDOSCOPE

BACKGROUND AND SUMMARY

Endoscopic instruments are widely known in which illumination of the field is provided by a fiberoptic cable or bundle that transmits light through the barrel of the endoscope to its distal end and in which visual images are then transmitted back to the physician through a series of lenses extending through the endoscope barrel from a field lens at the distal end to an eyepiece lens assembly at the endoscope's proximal end. The field lens commonly faces in a forward or longitudinal direction, although a forward-oblique orientation is often provided. Where lateral viewing is desired, the practioner must usually remove the endoscope from the patient and replace it with another endoscope having side-viewing capability. It is believed apparent that endoscopic procedures would be rendered more effective and efficient if a single endoscope could be arranged so that the user could switch at will between two views (forward and lateral) of the inspection site without removing the endoscope from the patient.

One aspect of this invention lies in the recognition of such a need and the further recognition that mechanical schemes for achieving such an objective would not be practical because the mechanisms would be too complicated, would occupy too much space, and would be nearly impossible to fabricate economically. Such considerations render unrealistic any construction in which, for example, an endoscope might be provided with a mechnically-steerable prism and field lens assembly, or with two field lenses in combination with a prism that is somehow moved mechanically as to direct one or the other of the two fields into the objective lens.

In brief, this invention involves the discovery that a relatively uncomplicated and highly-effective dual view endoscope may be achieved without any mechanical switching mechanism, or any separately movable parts, at the endoscope's distal end. Such results are accomplished by providing the endoscope with two fixed field lens assemblies at the endoscope's distal end, one assembly facing generally forwardly and the other laterally. Light received by the field lenses is directed through a beam combiner prism and then through an objective lens and a series of relay lenses back to the eyepiece lens assembly at the endoscope's proximal end. A control system is provided for selectively blocking the transmission of light received by either of the field lens assemblies while allowing the transmission of light received by the other of those assemblies. In one embodiment, the adjustable light transmission control means takes the form of polarizing filters for polarizing the light passing from the field lenses so that the orthological linear polarization of light from one of the field lens assemblies is at right angles to the polarization of light from the other assembly, and then providing the endoscope with an adjustable polarization-sensitive transmission filter interposed between the field lenses and the eyepiece for selectively blocking the transmission of polarized light from either one of the field lenses while transmitting polarized light from the other of such field lenses. In another embodiment, the light transmission control means takes the form of a pair of liquid crystal filters interposed between the respective field lenses and the beam combiner prism, each of the liquid crystal filters being capable of being electrically activated to permit light from only a selected one of the two field lenses to enter the beam combiner prism at any one time.

Where polarization is used for selectively controlling the transmission of an image from one field lens or the other, the light-polarizing means may comprise dichroic polarizers, or other suitable polarizing elements, at the exit faces of the field lenses. In a preferred form, selective polarization is produced by a multilayer dielectric reflector in the beam combiner prism. The polarization-sensitive transmission filter may take the form of a dichroic polarization filter, or a thin-film multilayer polarization filter, or a MacNeille prism. Ninety degree rotation of the filter or prism within the proximal end portion of the endoscope may be achieved by manually rotating an external collar that is mechnically or magnetically coupled to the polarization-sensitive transmission filter. Alternatively, that filter may be fixed within the endoscope and a twisted nematic liquid crystal cell having glass plate electrodes may be used for electrically controlling the transmission of an image from one field lens assembly or the other.

Other advantages, features, and objects of the invention will become apparent from the specification and drawings.

BRIEF DESCRIPTION OF DRAWINGS

FIG. 4 is a fragmentary sectional view similar to FIG. 3 but illustrating a modified arrangement for polarizing light from the field lenses.

FIG. 5 is a greatly enlarged schematic view of the interface between the elements of the beam combiner prism used in the modification of FIG. 4.

FIG. 6 is an enlarged fragmentary longitudinal sectional view of the proximal end of the instrument.

FIG. 7 is a cross sectional view taken along line 7—7 of FIG. 6.

FIG. 8 illustrates a dichroic polarization filter in combination with a twisted nematic liquid crystal cell for use as the switching means of this invention.

FIG. 9 illustrates modified switching means in the form of a MacNeille prism in combination with a twisted nematic liquid crystal cell.

FIG. 10 is a fragmentary sectional view illustrating the distal end of a simplified but functional dual view endoscope embodying the invention.

DETAILED DESCRIPTION OF PREFERRED EMBODIMENTS

Figure 2:
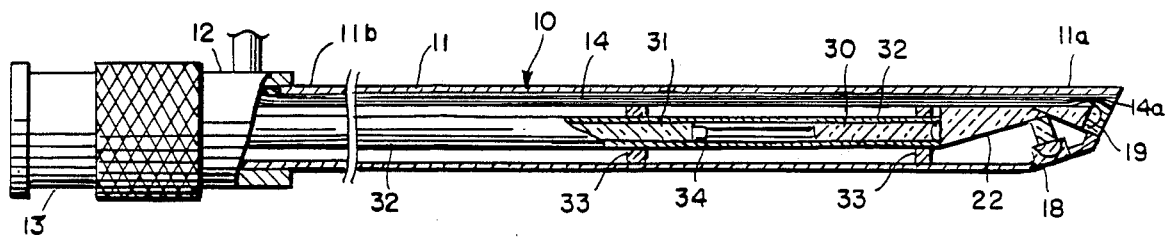
FIG. 2 is a sectional longitudinal view of the instrument.

Referring to the drawings, the numeral 10 generally designates an endoscope having an elongated outer tube or barrel 11 with distal and proximal ends 11a and 11b, respectively. While the barrel would ordinarily be formed of rigid material, it may be of flexible construction as disclosed in U.S. Pat. Nos. 4,148,550 and 4,148,551. The proximal end of the outer barrel is secured within a tubular housing 12 to which a standard image-magnifying eyepiece lens assembly 13 is connected. Illumination for the field of view is provided by a light-transmitting glass fiber bundle 14 that extends through substantially the full length of the outer barrel as shown in FIG. 2. The bundle is operatively connected to a conventional light source 15, and the distal end of the bundle 14a is exposed to illuminate the field of view at the barrel's distal end 11a.

Figure 3:
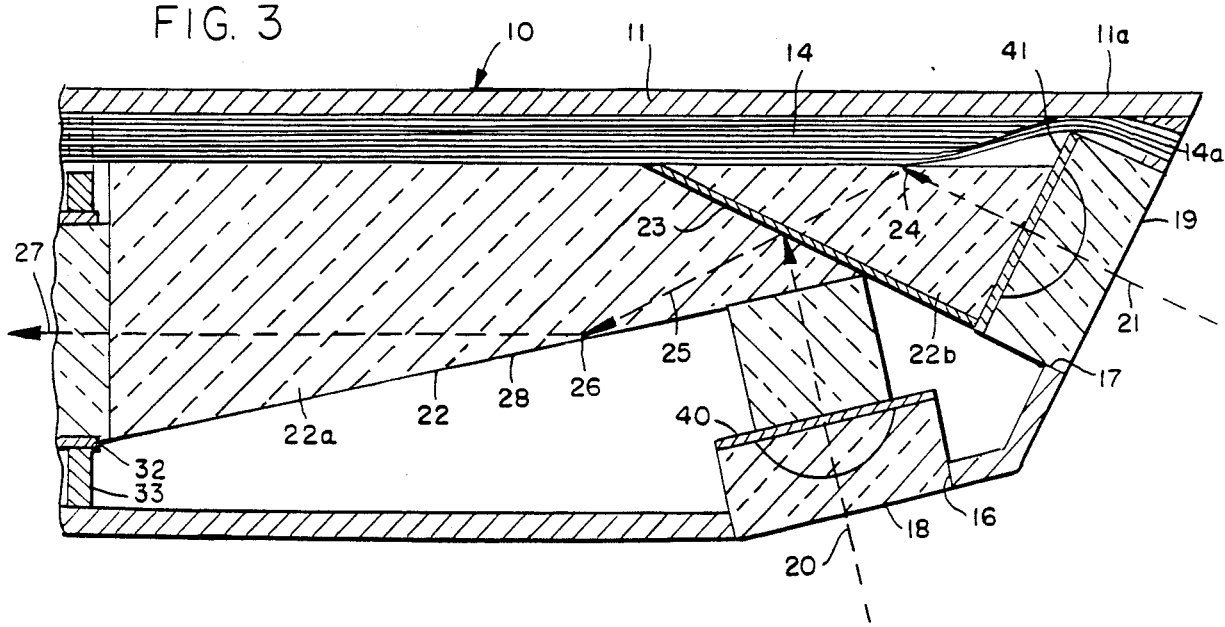
FIG. 3 is an enlarged fragmentary longitudinal sectional view of the distal end of the instrument.

Apertures 16 and 17 are provided in the distal end of the tubular barrel, and field lenses 18 and 19 are secured within those apertures as illustrated most clearly in FIG. 3. The orientation of the two field lenses may be varied considerably according to the operating requirements of the instrument and the preferences of users. Thus, the laterally-facing field lens 18 may be set at an angle within the range of 70° to 90° with respect to the longitudinal axis of the barrel (an angle of approximately 78° being shown), whereas the forwardly or distally facing field lens 19 may be set at an angle within the general range of 0° to 35° in relation to the same axis (an angle of about 26° being depicted). In general, for urological applications the locations of the two entrance apertures 16, 17, the angles of the chief rays for the field lenses, and the included cone angles of the ray bundles should be compatible with existing resectoscope and cystocope geometries so that the endoscope can fit into existing equipment without need to modify the equipment or replace it with special designs adapted for use with the dual view endoscope.

For clarity of illustration, FIG. 3 illustrates only the chief rays 20 and 21 through field lenses 18 and 19, respectively. Immediately adjacent the field lenses within the distal end of the tubular outer barrel 11 is a beam combiner prism (BCP) 22 for redirecting the rays from the field lenses so that both ray cones will travel along the same path through the objective lens and relay lens systems. The BCP 22 comprises two prism elements 22a and 22b having coplanar faces cemented or sealed together with a suitable reflective-transmissive coating 23 therebetween. As is well known in BCP design, such a coating may take the form of a thin (usually monomolecular) layer of aluminum or other suitable metal. The thickness of the aluminum layer is selected so that it reflects approximately half of the incident light and transmits the other half. Thus, in the configuration shown in FIG. 3, the light passing through field lens 19 follows the path of chief ray 21 where it undergoes a first internal reflection at 24 and is directed through coating 23 along light path 25. Approximately 50 percent of such light is transmitted by the coating and is again internally reflected at 26 where it is redirected proximally along the optical axis or axial light path 27 of the system. Similarly, light passing through the other field lens 18 is partially reflected and partially transmitted by coating 23, and the reflected moiety also follows path 25 and is internally reflected at 26 along the longitudinal axis of the lens system. It is to be noted that in each instance there is a double reflection of the rays from the field lenses as they pass through the BCP. Surface 28 of prism element 22a is both the entrance surface for the lateral rays from field lens 18 and the second reflecting surface for both the forward and the lateral rays. The most efficient way to accomplish this dual function is to leave surface 28 uncoated with the second reflection at 26 being due to total internal reflection. Total internal reflection is readily achieved because the angle of incidence on this surface for all rays will be large enough to insure achieving total internal reflection conditions with any of a wide variety of optical glasses. However, to avoid frustrating such total internal reflection, surface 28 must not be anti-reflection coated. Thus, there will be about a 5 percent Fresnel reflection loss for the lateral rays 20 entering the system at surface 28.

The BCP directs light along path 27 towards the eyepiece 13 through objective lens 30 and a series of relay lenses 31. As depicted in FIG. 2 the objective and relay lenses are supported within an inner tubular barrel 32 fixed within the outer barrel 11 by mounting elements 33. Tubular spacers 34 within the inner barrel space the lenses apart for the proper transmission of an image to the eyepiece assembly 13. The eyepiece lens assembly may be entirely conventional and includes a lens group for achieving a desired degree of magnification of the image.

Although the images from both the lateral view and the forward view follow the same path through the lens train to the eyepiece, means are provided for preventing more than one image from being transmitted to the viewer at any given time. In one embodiment of the invention, such selectively adjustable light transmission control means takes the form of light polarizing elements 40, 41 between the respective field lenses 18, 19 and BCP 22, plus an adjustable polarization-sensitive transmission filter 42 within housing 12 near eyepiece 13. The polarizing elements or layers 40 and 41 may be any conventional dichroic light polarizing means with the result that light from the lateral field entering BCP 22 will be polarized with its path axis at 90° with respect to the path axis of light entering the BCP from the forward field. Light from both fields therefore passes simultaneously along axis 27 towards the eyepiece but the light from the respective fields is encoded by polarization so that by selective adjustment of the polarization-sensitive transmission filter 42 only one image will be transmitted to eyepiece 13.

While such a system is highly effective in encoding the images so that a user may, by adjusting filter 42, select the desired image and reject the other image, the loss of light-transmitting efficiency produced by the combination of polarizers and beam combiner prism may in some instances be considered objectionable. Specifically, as already noted the BCP transmits only 50 percent of the incident light, reflecting the remaining 50 percent of such light. For an ideal polarizer, the transmission of a given polarization state cannot exceed 50 percent, and 30–35 percent is a common value for commercially-available thin dichroic polarizers. Consequently, in the system thus described, the overall transmission from each field lens 18, 19 to the objective lens 30 via the BCP cannot exceed 25 percent.

Such transmission loss may be reduced by the preferred embodiment depicted in FIGS. 4 and 5. The construction is identical to that shown in FIG. 3 except that the separate elements or encoding means 40, 41 are eliminated and a multilayer dielectric reflector 123 is substituted for the previously described reflective-transmissive metallic monolayer 23. The multilayer 123 performs both the polarizing functions of elements 40 and 41 and the beam-combining function of coating 23, but with greatly reduced loss of light transmission. Specifically, image brightness may be approximately tripled, for any given level of illumination, when compared with the brightness of the image produced by the embodiment of FIG. 3.

The multilayer 123 is constructed so that it reflects light polarized perpendicular to the plane of incidence (s polarization) and transmits light polarized in the plane of incidence (p polarization). The means for obtaining polarization selective reflection is similar to that described in U.S. Pat. No. 2,403,731, the disclosure of which is incorporated by reference herein.

Like FIG. 3, FIG. 4 depicts a double reflection BCP with the included angle between the chief rays 20 and 21 of the two beams at the field lenses being less than 90°. The component of the lateral beam 20 which is p polarized will pass through the multilayer dielectric deflector 123 and will pass entirely out of the system. The component of the same lateral beam 20 that is s polarized will be reflected by multilayer 123 and pass on through the endoscope to the eyepiece where it will be observed as the image of the lateral object field.

In analogous manner, the p polarized component of the forward beam 21 will pass through multilayer 123 and therefore on through the endoscope to the eyepiece where it will be observed as the image of the forward object field. The s polarized component of the forward beam will be reflected from the multilayer and pass out of the system (or into a suitable absorbing layer, not shown, along the external or upper surface of prism element 22b). Consequently, only p polarized light from the lateral image and s polarized light from the forward image will be transmitted through the objective and relay lenses towards the eyepiece. At the eyepiece end of the endoscope, the lateral object field will be polarized in a horizontal direction whereas the forward image field will be polarized in a vertical direction with respect to the viewer.

FIG. 5 schematically illustrates the multilayer dielectric reflector 123 which functions as a polarizing beam combiner. As shown, the beam combiner layers are deposited on prism element 22b and then, after coating, that prism element is joined by cement layer 124 to prism element 22a. For purposes of illustration, the multilayer is of the type (HL)$^m$H where m=2 and where H denotes a high index optically transparent material such as zinc sulfide with index $n_H$ and L denotes an index material such as cryolite with index $n_L$.

The indices of the prism glass and the H and L layers, $n_G$, $n_H$ and $n_L$, respectively, are selected so that Brewster's condition is satisfied at each of the dielectric interfaces for the appropriate angle of incidence. These angles are $\Theta_{GH}$ for the glass-high index interface, $\Theta_H$ for the high index low-index interfaces and the high index-glass interface, and $\Theta_L$ for the low index-high index interfaces. P polarized light incident upon a refracting interface at Brewster's Angle will pass through the interface with reflection. Consequently, a multilayer constructed as described will transmit p polarized light with very little loss and almost no reflection.

High reflection of s polarized light is obtained simultaneously with high transmission of p polarized light by setting the thickness of each thin film layer to $\lambda/4$ at the angle of propagation through the layer where $\lambda$ is the wavelength of light in the film layer. Broadband operation is obtained by optimizing one half of the multilayer stack for s polarized reflection at one wavelength and the other half of the multilayer for a different wavelength.

In this preferred system, utilizing a multilayer dielectric reflector 123 as the light polarizing means and as the coating for the beam combiner, the reflection of s polarized light and the transmission of p polarized light can exceed 90 percent. Hence, the overall transmission from field lens to objective lens via the BCP can be 45 percent or greater, a factor of 2 to 3 above that obtainable with separate polarizing elements 40, 41 and a partially-reflecting metallic monolayer 23. The total number of dielectric layers may range between 5 to 15 depending on factors such as the selected prism material (index $n_G$), the angle of incidence ($\Theta_{GH}$), the included angle of the light cone transmitted by the field lenses, the required polarization purity, the thin film optical coating materials used, and the spectral bandwidth. For an endoscope, the spectral bandwidth will usually be the visible spectrum from 0.5 microns in the ultraviolet to 0.76 microns in the near-infrared.

As previously indicated, the adjustable light transmission control means includes an adjustable polarization-sensitive transmission filter 42 within the endoscope housing 12 adjacent eyepiece lens assembly 13. The polarization-sensitive transmission filter 42 may be a high quality dichroic polarizer, a multilayer filter (as already described), or a MacNeille prism polarizer (as described in aforementioned U.S. Pat. No. 2,403,731). Means must be provided for supporting filter 42 so that it can be rotated at least 90° about its optical axis so that in one extreme of rotation the light transmitted to the eyepiece is s polarized and in the other extreme of rotation only p polarized light is transmitted to the eyepiece. Depending on which position of adjustment the rotatable filter is in, the viewer using the instrument will see either the lateral field or the forward field through the eyepiece.

FIGS. 6 and 7 illustrate a mechanical-magnetic coupling for manually rotating filter 42 into its selected positions of adjustment. The filter is supported within a tubular holder 50 that is coaxial with barrel 11 and eyepiece 13 and is carried by antifriction annular bearing elements 51 and 52 of Teflon or other suitable material. Magnet 53 is mounted upon the tubular holder 50 and a second magnet 54 is carried by control ring or sleeve 55 that is rotatably mounted upon the housing 12. By rotating the knurled external adjustment sleeve 90° in one direction or the other, the filter holder 50 will also rotate the same angular extent to alter the pass direction for filter 42 from p polarization to s polarization. A retention screw 56 not only prevents axial displacement of the sleeve upon housing 12, but also limits the extent of rotation of the sleeve because of the circumferential extent of slot 57 in which it is received.

Other means may be provided for achieving the desired rotation of filter pass direction which avoid the mechanical complications of physically rotating the polarization-sensitive transmission filter. FIG. 8 depicts a filter assembly 142 in the form of a dichroic polarizer 143 combined with a twisted nematic liquid crystal cell 144. FIG. 9 shows a similar twisted nematic crystal cell 144 in combination with a MacNeille prism 145 to form a filter assembly 142'. In both cases, filter assemblies 142 and 142' would be located in the position discussed with respect to filter 142 but would be fixed rather than rotatably mounted. (Rotating collar 55 may be retained as a switching element or other suitable switching means may be provided, as hereinafter described.) In each case, the fixed-position filter assembly 142, 142' would be oriented to pass p polarized light which, for the endoscope, is the forwardly-received image. The twisted nematic liquid crystal cell 144 consists of a thin layer 146 (approximately 10 microns) of suitable nematic liquid crystal material between two glass plates 147 and 148 coated on their interior facing surfaces with a transparent conducting layer and sealed at their edges. The interior cell surfaces are treated to cause the uniaxial optic axis of the liquid crystal molecules to lie nearly parallel to these surfaces. By rotating (during manufacture) the two glass plates about their common normal axis, it is possible to cause the nematic optical axis to undergo a smooth and continuous 90° twist in the plane of the glass plates from one boundary surface to the other.

Electrical leads (not shown) are provided to establish an alternating electric potential across the two transparent conducting electrodes (typically 5–6 volts, 60 Hertz, 10 microamperes). This establishes an electric field perpendicular to the glass plates and causes reorientation of the nematic molecules from orientation parallel to the plates to orientation parallel to the electric field (the "on" state).

In the absence of the alternating electric potential established across the transparent conducting electrodes (the "off" state), the twisted uniaxial molecular orientation of the nematic material causes the plane of polarization of an incident optical beam to rotate 90° in passing through the liquid crystal layer. In the "on" state, because the nematic molecules are reoriented by the applied electric field so as to resolve the twisted molecular structure, the polarization of an incident optical field does not change upon traversing the liquid crystal layer. Thus, the liquid crystal cell may be adjusted electrically to select between 2 polarized images. In the "on" state, the cell does not alter the state of polarization of the light transmitted to the polarizer 143, 145; consequently, when the cell is "on" the p polarized (i.e., forwardly-received) image is visible to the viewer. Conversely, when the cell is in its "off" state, the polarization of the light transmitted through the cell to the polarizer 143, 145 is rotated 90°; hence, s polarized light becomes p polarized light, and vice versa, and the lateral field of view is visible to the user.

In FIGS. 8 and 9, the liquid crystal cells 147 are not oriented normal to the incident light. The reason is that the apparent "untwisting" of the nematic material depends upon the angle of incidence. By orienting the cell at a slight angle in the range of 10° to 20° from the optical axis of the cell, the response of the system will be uniform over the included angle of the ray cone immerging from the eyepiece lens.

Figure 1:
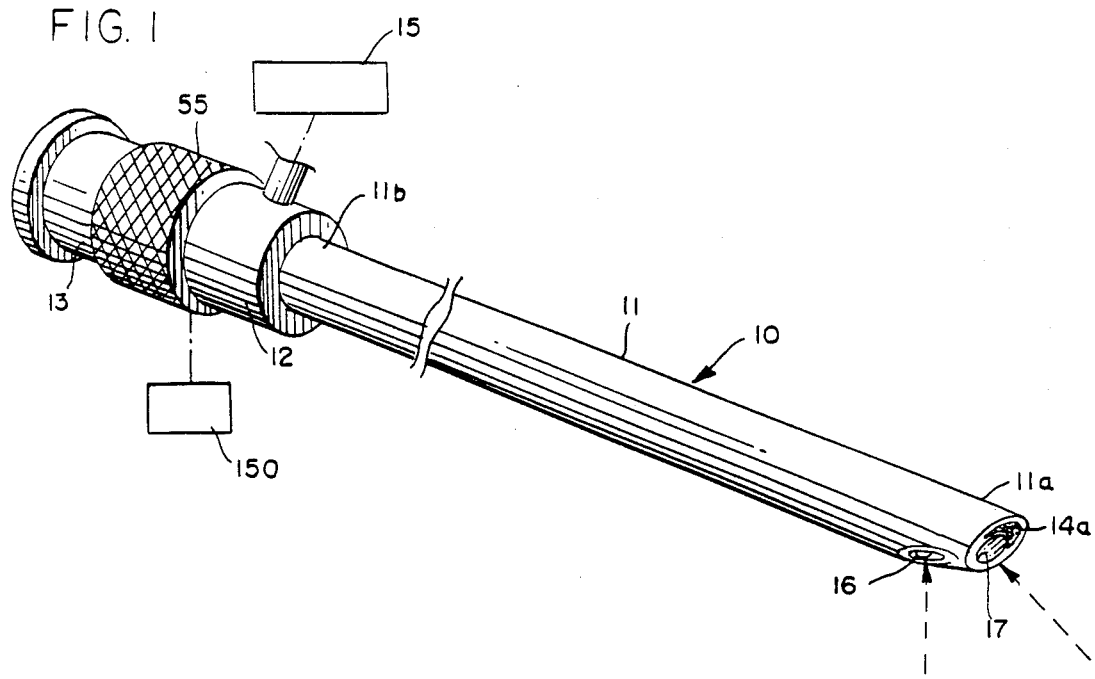
FIG. 1 is a perspective view of a dual-view endoscopic instrument embodying the invention.

Any suitable switching means may be provided for controlling the electrical field applied to filter assemblies 142, 142'. The rotatable control sleeve 55 and housing 12 may be provided with suitable contacts (not shown) with the sleeve connected to a suitable source of alternating electrical energy 150 diagramatically illustrated in FIG. 1, but it is to be understood that any other conventional switching means may be provided.

A further embodiment of the invention is identical to the construction as shown in FIG. 3 except that elements 40 and 41 take the form of liquid crystal filters or shutters. Such liquid crystal filters are well known in the art and may be either polarizing or non-polarizing. Electrical activation of each filter or shutter blocks the light from passing from the respective field lens into the BCP; hence, by selective activation of the liquid crystal filters, light from one field lens or the other (the lens associated with the unactivated filter) is allowed to pass to the eyepiece while the light associated with the activated filter is blocked. Since such liquid crystal filters control light entering the BCP from the field lenses, they also function as the adjustable light transmission control means, eliminating the need for a separate filter (such as 42) in the housing 12 of the endoscope.

As a further illustrative example, FIG. 10 depicts the distal end portion of a simplified dual view endoscope constructed in accordance with this invention. Dimensions a through i as represented in that drawing are as follows (in inches): a, 0.375; b, 0.118; c, 0.500; d, 0.615; e, 0.079; f, 0.210; g, 0.134; h, 0.038; i, 0.158. The right angle prism was formed of Schott SS-5 glass with its coplanar surfaces coated with a broadband (450 nm to 700 nm) polarizing multilayer as follows: $T_p > 0.99$; $R_p < 0.01$; $T_s < 0.01$; $R_s > 0.99$. A relay lens system composed of 3 relay lens cells each having a length of 2.22 bridged by spacers each having a length of 1.910 transmits the image through the barrel to the rotatable polarizing element and eyepiece. The eyepiece may be a 10×Ramsden eyepiece as commercially available.

While in the foregoing we have disclosed details of the invention in considerable detail for purposes of illustration, it will be understood that many of these details may be varied without departing from the spirit and scope of the invention.

We claim:

1. A dual view endoscope comprising an elongated outer tubular barrel having proximal and distal ends and having optical entrance apertures at its distal end; a first field lens mounted within said distal end of said barrel having an optical axis extending in a first direction for receiving light through one of said apertures; a second field lens mounted within said distal end having an optical axis extending in a second direction for receiving light through the other of said apertures; beam combining prism means adjacent said field lenses for directing light therefrom along a single path in a proximal direction; an eyepiece lens assembly at said proximal end of said barrel for the viewing of images transmitted thereto; objective and relay lens means along said barrel for producing images and transmitting the same to said eyepiece lens assembly; and adjustable light transmission control means for selectively blocking the transmission to said eyepiece lens assembly of light received by either one of said first and second field lenses while allowing the transmission to said eyepiece lens assembly of light received by the other of said field lenses.

2. The endoscope of claim 1 in which said adjustable light transmission means comprises a first liquid crystal filter interposed between said first field lens and said beam combining prism means, and a second liquid crystal filter interposed between said second field lens and said beam combining prism means; each of said liquid crystal filters being capable of being electrically activated to permit light from only a selected one of said first and second field lenses to enter said beam combining prism means at any one time.

3. The endoscope of claim 1 in which said adjustable light transmission control means comprises light polarizing means for polarizing the light from said field lenses so that the orthological linear polarization from said first field lens is at right angles to the orthological linear polarization from said second field lens; and an adjustable polarization-sensitive transmission filter interposed between said beam combining prism means and said eyepiece lens assembly for selectively blocking the transmission of polarized light from either one of said field lenses while transmitting polarized light from the other of said field lenses.

4. The endoscope of claim 3 in which said light polarizing means comprises a multilayer dielectric reflector within said beam combining prism means for simultaneously polarizing and combining the beams from said first and second field lenses.

5. The endoscope of claim 3 in which said light polarizing means comprises a pair of light polarizing filters between said first and second field lenses and said beam combining prism.

6. The endoscope of claim 3 in which said polarization-sensitive transmission filter is rotatably mounted in said barrel for rotation between a first position in which it transmits polarized light from said first field lens while blocking polarized light from said second field lens, and a second position in which it transmits polarized light from said second field lens while blocking polarized light from said first field lens.

7. The endoscope of claim 6 in which said polarization-sensitive transmission filter is a dichroic polarization filter.

8. The endoscope of claim 6 in which said polarization-sensitive transmission filter is a multilayer polarization filter.

9. The endoscope of claim 6 in which said polarization-sensitive transmission filter is a MacNeille prism.

10. The endoscope of claim 3 in which said polarization-sensitive transmission filter is fixed within said barrel and comprises a dichroic polarization filter and a twisted nematic liquid crystal cell having glass plate electrodes; and means for establishing an alternating electrical potential across said electrodes.

11. The endoscope of claim 10 in which said polarization-sensitive transmission filter is fixed within said barrel and comprises a MacNeille prism and a twisted nematic liquid crystal cell having glass plate electrodes; and means for establishing an alternating electrical potential across said electrodes.

12. The endoscope of claim 6 in which an external control ring is rotatably mounted upon said barrel adjacent said eyepiece lens assembly; and means operatively coupling said polarization-sensitive transmission filter and said control ring for simultaneous rotation.

13. The endoscope of claim 12 in which said means for operatively coupling said polarization-sensitive transmission filter and said control ring comprises magnetic means.

14. The endoscope of claim 1 in which said first field lens faces distally and said second field lens faces laterally.

15. The endoscope of claim 14 in which said first field lens faces distally at an oblique angle of no more than 35° with respect to the longitudinal axis of said barrel.

16. The endoscope of claim 14 in which said second field lens faces laterally and distally at an angle within the range of 70° to 90° with respect to the longitudinal axis of said barrel.

17. The endoscope of claim 1 in which a fiberoptic light-transmitting bundle extends through said barrel for transmitting light to said distal end for illuminating an external field viewed by said field lenses.

18. The endoscope of claim 1 in which said beam combining prism means comprises two double-reflection beam combining prism elements having a pair of coplanar faces cemented together with light reflective/transmissive means disposed therebetween.

19. The endoscope of claim 18 in which said light reflective/transmissive means comprises a thin metallic layer capable of reflecting a portion of the light, and transmitting another portion of the light, from each of said field lenses.

20. The endoscope of claim 19 in which said light reflective/transmissive means is a multilayer dielectric reflector.

* * * * *